United States Patent
Mezger et al.

(10) Patent No.: US 11,495,342 B2
(45) Date of Patent: Nov. 8, 2022

(54) PLANNING AN EXTERNAL VENTRICLE DRAINAGE PLACEMENT

(71) Applicant: Brainlab AG, Munich (DE)

(72) Inventors: Uli Mezger, Kirchheim (DE); Rainer Birkenbach, Erding (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 16/477,721

(22) PCT Filed: Aug. 23, 2018

(86) PCT No.: PCT/EP2018/072773
§ 371 (c)(1),
(2) Date: Jul. 12, 2019

(87) PCT Pub. No.: WO2019/063215
PCT Pub. Date: Apr. 4, 2019

(65) Prior Publication Data
US 2019/0371451 A1    Dec. 5, 2019

Related U.S. Application Data

(63) Continuation-in-part of application No. PCT/EP2017/074363, filed on Sep. 26, 2017.

(51) Int. Cl.
*G16H 20/40* (2018.01)
*G16H 10/60* (2018.01)
(Continued)

(52) U.S. Cl.
CPC .......... *G16H 20/40* (2018.01); *G16H 10/60* (2018.01); *G16H 30/20* (2018.01); *G16H 30/40* (2018.01)

(58) Field of Classification Search
CPC ........ G16H 20/40; G16H 10/60; G16H 30/20; G16H 30/40
(Continued)

(56) References Cited

U.S. PATENT DOCUMENTS

2007/0249911 A1    10/2007   Simon
2008/0123922 A1*   5/2008    Gielen ................ A61B 5/06
                                                          345/629
(Continued)

FOREIGN PATENT DOCUMENTS

EP    1563799 A1   8/2005
EP    3529808      8/2019
(Continued)

OTHER PUBLICATIONS

Muirhead, William R. et al., Trajectories for frontal external ventricular drain placement: virtual cannulation of adults with acute hydrocephalus, British Journal of Neurosurgery, 26(5): pp. 710-716, Oct. 2012.
(Continued)

*Primary Examiner* — Robert W Morgan
*Assistant Examiner* — Rachel F Durnin
(74) *Attorney, Agent, or Firm* — Middleton Reutlinger (57) ABSTRACT

Disclosed medical data processing method for planning an external ventricle drainage placement, wherein the method comprises executing, on at least one processor (3) of at least one computer (2), the following steps: a) patient image data describing at least one image of an anatomical structure of a patient is acquired (S1); b) atlas data describing a model of the anatomical structure is acquired (S2); c) mapping data describing a mapping of the patient image data to the atlas data is determined (S3); d) spatial relationship data is acquired (S4) which describes a predetermined spatial relationship between at least one potential trajectory for placing the external ventricle drainage in the anatomical structure on the one hand and a surface of the anatomical structure on the other hand; e) entry point data is determined (S5) which describes the position of an entry point (13) of the external
(Continued)

ventricle drainage on the surface of the anatomical structure based on the mapping data and the spatial relationship data.

13 Claims, 4 Drawing Sheets

(51) Int. Cl.
*G16H 30/20* (2018.01)
*G16H 30/40* (2018.01)

(58) Field of Classification Search
USPC .......................................................... 705/2–3
See application file for complete search history.

(56) References Cited

U.S. PATENT DOCUMENTS

2017/0065349 A1* 3/2017 Ourselin ................. A61B 34/10
2019/0209245 A1* 7/2019 Sparks .................. G06T 19/003

FOREIGN PATENT DOCUMENTS

| WO | WO-2017028934 A1 * | 2/2017 | ............. A61B 34/10 |
| WO | WO2017028934 A1 | 2/2017 | |
| WO | 2019063215 | 4/2019 | |

OTHER PUBLICATIONS

International Search Report and Written Opinion for PCT Application No. PCT/EP2018/072773 dated Dec. 7, 2018.

\* cited by examiner

Fig. 4

PLANNING AN EXTERNAL VENTRICLE DRAINAGE PLACEMENT

The present invention relates to a medical data processing method for planning an external ventricle drainage placement, a corresponding computer program, a non-transitory program storage medium storing such a program and a computer for executing the program, as well as a system for planning an external ventricle drainage placement.

TECHNICAL BACKGROUND

The placement of an external ventricle drainage is an important neurosurgical procedure. Usually rough guidelines are followed, in order to find the optimal entry point and trajectory for placing the external ventricle drainage, for example, palpate Bregma, go about 4 cm laterally and aim the trajectory towards ipsilateral canthus. The respective distances are usually measured by means of a conventional measurement tape arranged on the skin of the patient.

However, such rough guidelines do not take the individual ventricle anatomy into account. Furthermore, aligning the trajectory is quite difficult and often leads to suboptimal placement or multiple passes.

Computer assisted navigation is one approach for improving the accuracy of an external ventricle drainage placement. Nevertheless, the effort to setup the computer assisted navigation is often considered to be to high compared to its benefit. Moreover, placement of an external ventricle drainage is frequently conducted at the bedside, for example in an neuro intensive care unit, where computer assisted navigation is often not available.

The present invention allows for planning an external ventricle drainage which significantly improves the accuracy and safety of the procedure. Furthermore, the individual patient anatomy is considered for placing an external ventricle drainage. Moreover, computer assisted navigation, in particular a cumbersome setup and high costs associated with computer assisted navigation, may be avoided.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses acquiring patient image data describing at least one image of an anatomical structure of a patient. Moreover, atlas data describing an image-based model of the anatomical structure is acquired. A mapping of the patient image data to the atlas data is performed. By considering a predetermined spatial relationship between at least one potential trajectory for placing the external ventricle drainage in the anatomical structure on the one hand and a surface of the anatomical structure on the other hand an optimal entry point as well as an optimal trajectory for placing the external ventricle are determined based on the mapping.

General Description of the Present Invention

In this section, a description of the general features of the present invention is given for example by referring to possible embodiments of the invention.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The disclosed method provides, in a first aspect, a medical data processing method for planning an external ventricle drainage placement. In one example, the external ventricle drainage is a catheter.

The method comprises executing, on at least one processor of at least one computer, the following exemplary steps which are executed by the at least one processor.

In an (for example first) exemplary step, patient image data describing at least one image of an anatomical structure of a patient is acquired. In one embodiment, the patient image data is acquired by means of computed tomography, magnetic resonance tomography or ultrasound imaging. In contrast to the use of computer assisted navigation, no special 3D magnetic resonance images or special computed tomography sequences are required. In one example, standard medical imaging methods suffice. Nevertheless, the patient image data may also be acquired by means of 2D/3D modalities, angiography, fluoroscopy (with or without contrast agent), functional magnetic resonance imaging or diffusion magnetic resonance imaging. In one example, the patient image data may be acquired by means of the imaging methods mentioned in the section "Definitions" below.

The patient image data may describe structural information of an anatomical structure of a patient. In one example, the patient image data describes at least part of a patient's head.

In one embodiment, the patient image data comprises color values, which define the appearance and/or the information content of the image. In one example, the color values are multicolor color values (which are defined for example in the RGB color space). In another example, the color values are greyscale color values.

In one example, the patient image data allows for a differentiation between different parts (for example, different types of tissue) of the anatomical structure. Different types of tissue may be characterized by associated different color values.

In an (for example second) exemplary step, atlas data describing a model (for example, an image-based model) of the anatomical structure is acquired. For example, the atlas data comprises information about the identity (i.e. anatomical classification) of certain parts of the (for example, image-based) model. In one example, the atlas data comprises image information (for example positional image information) which can be matched (for example, by applying an elastic or rigid image fusion algorithm) for example to image information (for example, positional image information) contained in the patient image data so as to for example compare the atlas data to the patient image data, in order to determine the position of a certain part (for example, a landmark) of the anatomical structure in the patient image data which corresponds to the part of the anatomical structure defined by the atlas data. In one example, the atlas data comprises information about at least one anatomical landmark (for example, information about the identity of at least one anatomical landmark).

In an (for example third) exemplary step, mapping data describing a mapping of the patient image data to the atlas data is determined. For example, a mapping describes a transformation (for example, linear transformation) of an element (for example, a pixel or voxel), for example the position of an element, of a first data set (for example, the patient image data) in a first coordinate system to an element (for example, a pixel or voxel), for example the position of an element, of a second data set (for example, the atlas data) in a second coordinate system (which may have a basis which is different from the basis of the first coordinate system). In one embodiment, the mapping is determined by comparing (for example, matching) the color values (for example grey scale values) of the respective elements by means of an elastic or rigid fusion algorithm (cf. section "Definitions" below). The mapping is embodied for example by a transformation matrix (such as a matrix defining an affine transformation). In one embodiment, patient image data acquired by means of 2D magnetic resonance imaging is mapped to the atlas data, wherein the mapping is embodied by an affine transformation.

In an (for example fourth) exemplary step, spatial relationship data is acquired which describes a predetermined spatial relationship between at least one potential (for example, allowed) trajectory for placing the external ventricle drainage in the anatomical structure on the one hand and a surface of the anatomical structure on the other hand. In one embodiment, the spatial relationship data may describe a boundary condition for the position of a potential trajectory with regard to the position of a surface of the anatomical structure. For example, the term "position" comprises location and orientation.

A trajectory for placing the external ventricle drainage may be represented by a straight line comprising the entry point and the target point of the external ventricle drainage (for example, a tip of the external ventricle drainage). In one example, a trajectory for placing the external ventricle drainage is considered as a potential (for example, allowed) trajectory, if it fulfills a boundary condition described by the spatial relationship data.

In one example, the spatial relationship data may be extracted from the atlas data. In another example, the spatial relationship data may be extracted from a separate data set. In one example, a potential trajectory for placing the external ventricle drainage extends from an entry point (for example, allowed entry point) of the external ventricle drainage (for example, a tip of the external ventricle drainage) to a target point (for example, predefined target point) of the external ventricle drainage (for example, a tip of the external ventricle drainage).

In one embodiment, the spatial relationship data comprises information about at least one of a restricted area on the surface of the anatomical structure (for example, the skin) or a predefined angle of the potential trajectory (for example, a potential trajectory being represented by a straight line) to the surface of the anatomical structure. In one example, the restricted area may be defined by connecting a plurality of (for example, predetermined) points on the surface of the anatomical structure (for example, the skin). The points may be determined manually or automatically. In one example, a plurality of restricted areas may be defined.

In one example, an entry point of the potential trajectory is considered as an allowed entry point if the position of the entry point is comprised within the restricted area. In other words, an entry point whose position is outside the restricted area may not be allowed.

In one example, the information about the restricted area describes the position and/or size of the restricted area in relation to at least one anatomical landmark (for example, the position of an anatomical landmark). The information about the restricted area may describe the position and size of the restricted area on the patient's skin. The information about the at least one restricted area may be extracted from the atlas data. In one example, the information about the at least one restricted area may be defined (for example, predefined) based on the atlas data.

In one embodiment, the position and/or size of the restricted area is defined (for example, predefined) in relation to the position of at least one anatomical landmark. In one example, the size of the restricted area is predefined (for example, fixed). The position and/or the size of the restricted area may be fixed, set automatically or manually. In one example, the restricted area is defined (for example, predefined) as an area, for example quadrant, arranged before the coronal suture (anterior to the coronal suture). In one example, the restricted area does not touch (for example, overlap) a line extending from the nasion to the bregma. The restricted area may be arranged left or right to a line extending from the nasion to the bregma. In one example, the restricted area is defined as an area which is arranged before the coronal suture (anterior to the coronal suture) and does not touch (for example, overlap) a line extending from the nasion to the bregma.

In one embodiment, the predefined angle of the potential trajectory to the surface of the anatomical structure is in the range of 75° to 105°. In another embodiment, the predefined angle of the potential trajectory to the surface of the anatomical structure is in the range of 85° to 95°. In one example, the predefined angle of the potential trajectory to the surface of the anatomical structure is (substantially) perpendicular. In one example, the potential trajectory extends as a straight line.

In an (for example fifth) exemplary step, entry point data is determined which describes the position of an entry point (for example, optimal entry point) of the external ventricle drainage (for example, a tip of the external ventricle drainage) on the surface of the anatomical structure based on the mapping data and the spatial relationship data. In one example, the spatial relationship data defines at least one constraint for determining the entry point data (see above). By means of the at least one constraint the load upon a system for determining the entry point data may be reduced significantly.

By determining the position of an optimal entry point the risk of damaging critical tissue may be reduced. Furthermore, the (for example, final) position of the external ventricle drainage (for example, a tip of the external ventricle drainage) in a ventricle may be optimized with regard to an improved drainage.

In one example, the entry point data is output to an output device, for example a display device. Accordingly, an optimal entry point for the external ventricle drainage placement may be visualized (for example, on a mapped image of the anatomical structure) for the user in the patient coordinate system. Therefore, the use of a computer assisted navigation system may be avoided.

In one example, the entry point data comprises information about a spatial relationship of the entry point to a predetermined anatomical landmark of the anatomical structure. In one example, the spatial relationship is represented by the surface distance between the entry point and the point of intersection between the midline extending from the nasion to the bregma on the one hand and a line representing the surface distance between the entry point and the midline on the other hand (wherein the midline and the line representing the surface distance between the entry point and the midline are orthogonal to each other). Accordingly, the entry point data provides information about an optimal entry point in the patient coordinate system. In one example, the entry point may be represented by a vector relative to the position of an anatomical landmark in the patient coordinate system.

In one embodiment, the method further comprises the step of: safety region data is acquired which describes a region of the anatomical structure through which the potential trajectory is not allowed to extend, wherein the entry point data is determined based on the mapping data, the spatial relationship data and the safety region data. Accordingly, injury to sensitive parts of the anatomical structure may be avoided.

In one example, the safety region data describes a volume within the anatomical structure. In one example, the safety region data describes a volume containing at least one vessel and/or at least one sulcus cerebri. The safety region data may be extracted from the atlas data. In one example, the safety region may be defined manually. In one example, the safety region data defines another constraint (besides the at least one constraint defined by the spatial relationship data) for determining the entry point data.

In one embodiment, the method comprises the step of: trajectory data is determined based on the entry point data and a predefined position of a target point wherein the trajectory data describes a planned (for example, optimal) trajectory extending from the entry point of the external ventricle drainage to the target point. In one example, the predefined position of the target point corresponds to a region of interest. The predefined position of the target point may be extracted from the atlas data. The position of the target point may be predefined manually or automatically (for example, based on the patient image data, the atlas data and the mapping data). In one example, the planned trajectory is a (for example, optimized) trajectory comprising the (optimized) entry point whose position is described by the determined entry point data.

In one example, the method comprises the step of: the trajectory data is output to an output device, for example a display device. For example, the position of a trajectory (for example, relative to an anatomical landmark) may be output. For example, the length of the trajectory may be output. In one embodiment, the trajectory data is represented by a trajectory depicted in an image (for example, 2D image or 3D image) of the anatomical structure. Accordingly, a (for example, optimal) trajectory for the external ventricle drainage placement may be visualized (for example, on a mapped image of the anatomical structure) for the user in the patient coordinate system. Therefore, the use of a computer assisted navigation system may be avoided.

In one embodiment, the entry point data and/or the trajectory data may be visualized on an image-based model of the anatomical structure (for example, on a 2D or 3D skin model of the patient). In one example, the user may adapt the trajectory (for example, the target point of the trajectory) and the entry point is updated automatically.

In a second aspect, the invention is directed to a computer program which, when running on at least one processor (for example, a processor) of at least one computer (for example, a computer) or when loaded into at least one computer (for example, a computer) of at least one computer (for example, a computer), causes the at least one computer to perform the above-described method according to the first aspect and/or to a (physical, for example electrical, for example technically generated) signal wave, for example a digital signal wave, carrying information which represents the program, for example the aforementioned program, which for example comprises code means which are adapted to perform any or all of the method steps described herein.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the at least one processor or is loaded into the at least one memory, or wherein the at least one computer comprises the program storage medium according to the third aspect.

In a fifth aspect, the invention is directed to system for planning an external ventricle drainage placement, the system comprising:
a) at least one medical imaging device for acquiring patient image data; and
b) the at least one computer according to the according to the fourth aspect,
wherein the at least one computer is operably coupled to the at least one medical imaging device for acquiring, from the at least one medical imaging device, the patient image data.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Within the framework of the invention, computer program elements can be embodied by hardware and/or software (this includes firmware, resident software, micro-code, etc.).

Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

For example, a mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

DESCRIPTION OF THE FIGURES

In the following, the invention is described with reference to the appended figures which represent a specific embodiment of the invention. The scope of the invention is however not limited to the specific features disclosed in the context of the figures, wherein.

Figure 1:
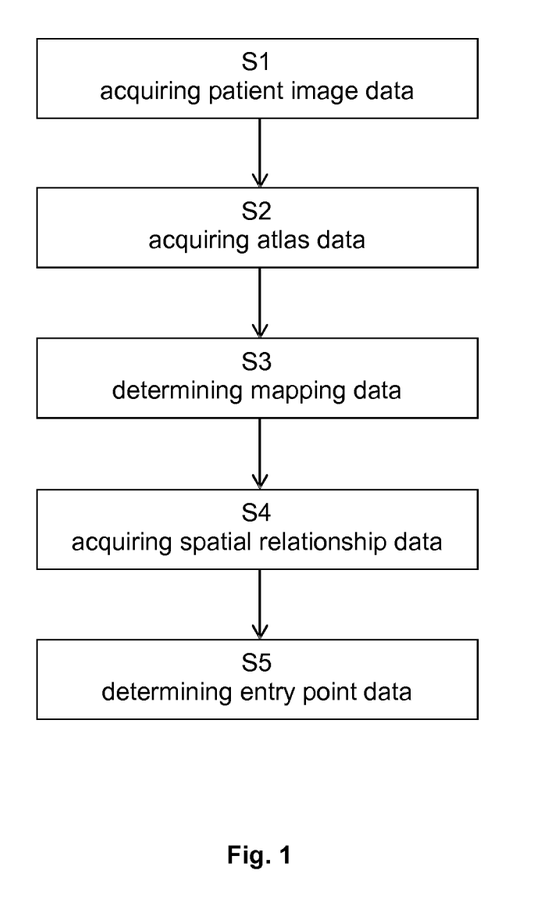
FIG. 1 is a flow diagram showing the basic steps of the disclosed method.

FIG. 1 is a flow diagram illustrating the basic steps of the disclosed method which in the illustrative example of FIG. 1 starts with a step S1 of acquiring patient image data describing at least one image of an anatomical structure of a patient. Then, step S2 is executed, which encompasses acquiring atlas data describing a (for example, image-based) model of the anatomical structure. In subsequent step S3 mapping data describing a mapping of the patient image data to the atlas data is determined. In step S4 spatial relationship data is acquired which describes a predetermined spatial relationship between at least one potential trajectory for placing the external ventricle drainage in the anatomical structure on the one hand and a surface of the anatomical structure on the other hand. The last step shown in FIG. 1 is step S5, which is directed to determining entry point data which describes the position of an entry point of the external ventricle drainage on the surface of the anatomical structure based on the mapping data and the spatial relationship data.

Figure 2:
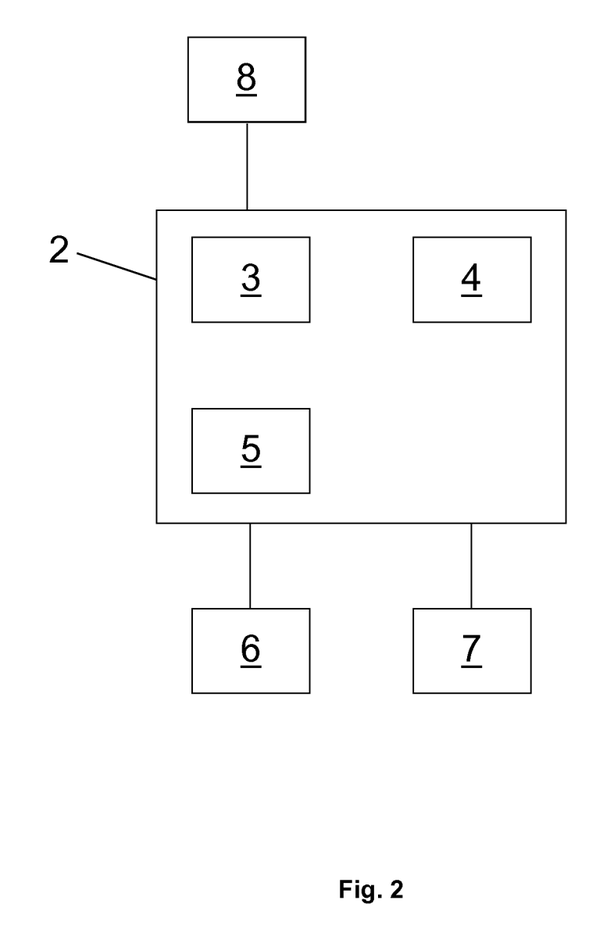
FIG. 2 is a schematic view of a system performing the disclosed method.

FIG. 2 shows an exemplary system for performing the disclosed method. The system comprises a computer 2 as well as a medical imaging device 8 operably coupled to the computer 2. The computer 2 comprises a processor 3, a memory 4 and an interface 5. The computer 2 is connected to an input unit 6, such as a mouse, a keyboard or a touch-sensitive surface, and an output unit 7 such as a display device, a speaker or a tactile sensation generation unit.

A program causing the computer 2 to perform the disclosed method may be loaded into the memory 4 of the computer. In one embodiment the program may be stored on a program storage medium comprised in or connected to the computer 2. Furthermore, the computer 2 may be operably coupled to at least one electronic data storage device for storing atlas data.

Figure 3:
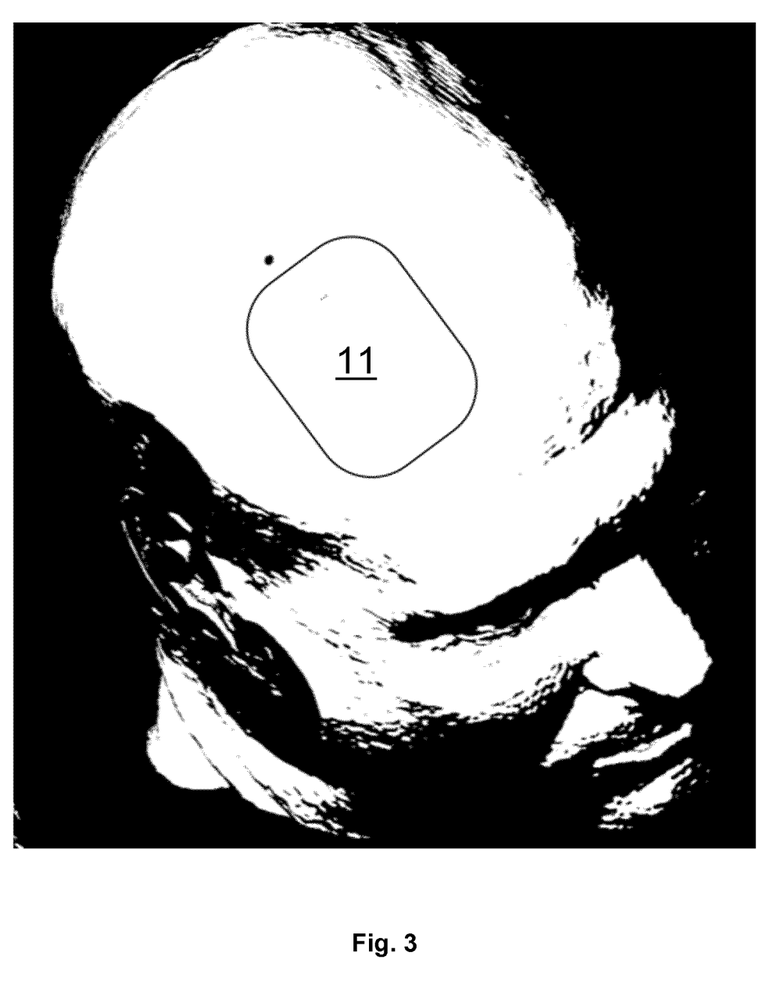
FIG. 3 is a perspective view of an image-based model of an anatomical structure showing a restricted area.

FIG. 3 is a perspective view of an image-based model of an anatomical structure (here a 3D skin model of a patient's head). FIG. 3 shows a restricted area 11 for which an entry point of a potential trajectory for placing the external ventricle drainage is allowed. Information about the position and the size of the restricted area 11 is comprised in the spatial relationship data. For example, the position and/or size of the restricted area 11 is predefined in relation to the position of at least one anatomical landmark. Here, for example, the restricted area is predefined to be arranged before the coronal suture (anterior to the coronal suture). Furthermore, for example, the restricted area is predefined as an area which does not overlap a line 25 extending from the nasion 23 to the bregma 21 (as shown in FIG. 4).

Figure 4:
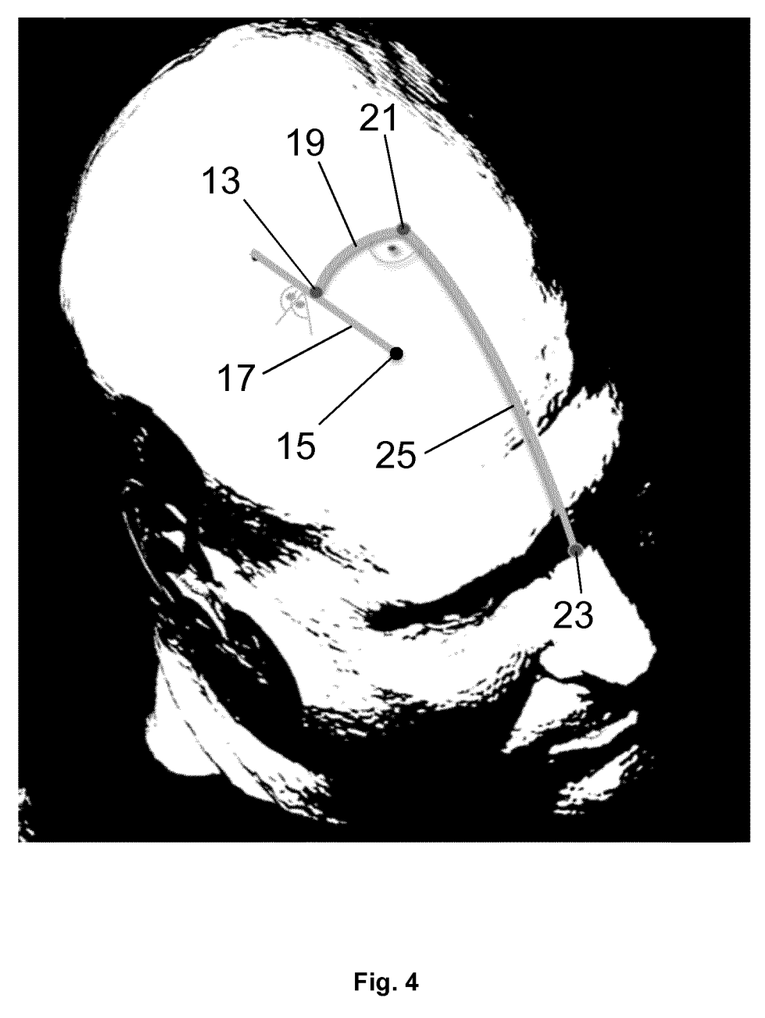
FIG. 4 is a perspective view of an image-based model of an anatomical structure showing an entry point for an external ventricle drainage placement.

In FIG. 4 an (optimal) entry point 13 (whose position is described by the determined entry point data) and a target point 15 (whose position is predefined based on the patient image data, the atlas data and the mapping data) of the external ventricle drainage is shown. The position of the (optimal) entry point 13 may be described as a function of a surface distance (distance on the skin which can be measured by a conventional measurement tape) to a predetermined anatomical landmark in the patient's coordinate system.

Midline 25 in FIG. 4 represents the surface distance between the bregma 21 and the nasion (for example 12.4 cm). Line 19 in FIG. 4 represents the surface distance (orthogonal relationship) between the entry point 13 and the midline 25 (for example 3.4 cm). Line 17 between the entry point 13 and the target point 15 represents a planned trajectory for the external ventricle drainage placement. As indicated by FIG. 4, the planned trajectory is orthogonal to the surface of the anatomical structure (here skin of the patient's head). The whole of line 17 represents the length of the ventricle drainage (for example 6.6 cm).

The invention claimed is:

1. A computer implemented method for planning an external ventricle drainage placement, wherein the method comprises executing, on at least one processor of at least one computer:
   acquiring patient image data describing at least one image of an anatomical structure of a patient, the anatomical structure including at least part of the patient's head;
   acquiring atlas data describing a model of the anatomical structure;

determining, by the at least one processor, mapping data describing a mapping of the patient image data to the atlas data, wherein determining the mapping data further includes:
- transforming, by the at least one processor, one of the patient image data or the atlas data, wherein the anatomical structure is at a same position as the other of the patient image data or atlas data,
- wherein the patient image data, represented by at least one of a pixel or a voxel, in a first coordinate system, is mapped to the atlas data, represented by at least one of a pixel or a voxel, in a second coordinate system that is different from the first coordinate system, to generate a 3D skin model of the patient's head, and
- wherein transforming the patient image data or the atlas data results in an optimum degree of similarity;

acquiring spatial relationship data which describes a predetermined spatial relationship between at least one potential trajectory for placing the external ventricle drainage in the anatomical structure and a surface of the anatomical structure;

determining, by the at least one processor, entry point data which describes the position of an entry point of the external ventricle drainage on the surface of the anatomical structure based on the mapping data and the spatial relationship data,
- wherein the position of the entry point is determined as a surface distance on the 3D skin model of the patient's head in an orthogonal relationship to a line extending from a bregma to a nasion in the patient's coordinate system; and preparing, by the at least one processor for output presentation to a user the visualization of the determined entry point data for placement of the external ventricle drainage.

2. The method according to claim 1, wherein the spatial relationship data comprises information describing at least one of a restricted area on the surface of the anatomical structure or a predefined angle of the potential trajectory to the surface of the anatomical structure.

3. The method according to claim 2, wherein the information describing the restricted area describes the position of the restricted area in relation at least one anatomical landmark and the size of the restricted area.

4. The method according to claim 2, wherein the predefined angle of the potential trajectory to the surface of the anatomical structure is in the range of 85° to 95°.

5. The method according to claim 2, wherein the entry point data comprises information describing a spatial relationship of the entry point to a predetermined anatomical landmark of the anatomical structure.

6. The method according to claim 2, further comprising:
acquiring safety region data which describes a region of the anatomical structure through which the potential trajectory is not allowed to extend;
wherein the entry point data is determined based on the mapping data, the spatial relationship data and the safety region data.

7. The method according to claim 2, wherein the method further comprises outputting the visualization of the entry point data to is output to a display device.

8. The method according to claim 2, further comprising determining trajectory data based on the entry point data and a predefined position of a target point wherein the trajectory data describes a planned trajectory extending from the entry point of the external ventricle drainage to the target point.

9. The method according to claim 8, further comprises outputting the trajectory data to a display device.

10. The method according to claim 2, wherein the patient image data is acquired by means of computed tomography, magnetic resonance tomography or ultrasound imaging.

11. A non-transitory computer-readable program storage medium comprising instructions which, when executed by at least one processor on at least one computer, causes the computer to:
acquire patient image data describing at least one image of an anatomical structure of a patient, the anatomical structure including at least part of the patient's head;
acquire atlas data describing a model of the anatomical structure;
determine mapping data describing a mapping of the patient image data to the atlas data, wherein determining the mapping data further includes:
- transforming, by the at least one processor, one of the patient image data or the atlas data, wherein the anatomical structure is at a same position as the other of the patient image data or atlas data,
- wherein the patient image data, represented by at least one of a pixel or a voxel, in a first coordinate system, is mapped to the atlas data, represented by at least one of a pixel or a voxel, in a second coordinate system that is different from the first coordinate system, to generate a 3D skin model of the patient's head, and
- wherein transforming the patient image data or the atlas data results in an optimum degree of similarity;

acquire spatial relationship data which describes a predetermined spatial relationship between at least one potential trajectory for placing the external ventricle drainage in the anatomical structure and a surface of the anatomical structure;

determine entry point data which describes the position of an entry point of the external ventricle drainage on the surface of the anatomical structure based on the mapping data and the spatial relationship data,
- wherein the position of the entry point is determined as a surface distance on the 3D skin model of the patient's head in an orthogonal relationship to a line extending from a bregma to a nasion in the patient's coordinate system; and prepare for output presentation to a user the visualization of the determined entry point data for placement of the external ventricle drainage.

12. At least one computer, comprising at least one processor and at least one associated memory, the memory storing instructions which, when executed by the at least one processor, causes the at least one processor to:
acquire patient image data describing at least one image of an anatomical structure of a patient, the anatomical structure including at least part of the patient's head;
acquire atlas data describing a model of the anatomical structure;
determine mapping data describing a mapping of the patient image data to the atlas data, wherein determining the mapping data further includes:
- transforming, by the at least one processor, one of the patient image data or the atlas data, wherein the anatomical structure is at a same position as the other of the patient image data or atlas data,
- wherein the patient image data, represented by at least one of a pixel or a voxel, in a first coordinate system, is mapped to the atlas data, represented by at least one of a pixel or a voxel, in a second coordinate system that is different from the first coordinate system, to generate a 3D skin model of the patient's head, and wherein transforming the patient image data or the atlas data results in an optimum degree of similarity;

acquire spatial relationship data which describes a predetermined spatial relationship between at least one potential trajectory for placing the external ventricle drainage in the anatomical structure and a surface of the anatomical structure;

determine entry point data which describes the position of an entry point of the external ventricle drainage on the surface of the anatomical structure based on the mapping data and the spatial relationship data, wherein the position of the entry point is determined as a surface distance on the 3D skin model of the patient's head in an orthogonal relationship to a line extending from a bregma to a nasion in the patient's coordinate system; and prepare for output presentation to a user the visualization of the determined entry point data for placement of the external ventricle drainage.

13. A system for planning an external ventricle drainage placement, the system comprising:

at least one medical imaging device for acquiring patient image data;

at least one computer, having at least one processor with associated memory, the associated memory having instructions which when executed by the at least one processor, performs the steps of:

acquiring patient image data describing at least one image of an anatomical structure of a patient, the anatomical structure including at least part of the patient's head;

acquiring atlas data describing a model of the anatomical structure;

determining mapping data describing a mapping of the patient image data to the atlas data, wherein determining the mapping data further includes:

transforming, by the at least one processor, one of the patient image data or the atlas data, wherein the anatomical structure is at a same position as the other of the patient image data or atlas data, wherein the patient image data, represented by at least one of a pixel or a voxel, in a first coordinate system, is mapped to the atlas data, represented by at least one of a pixel or a voxel, in a second coordinate system that is different from the first coordinate system, to generate a 3D skin model of the patient's head, and wherein transforming the patient image data or the atlas data results in an optimum degree of similarity;

acquiring spatial relationship data which describes a predetermined spatial relationship between at least one potential trajectory for placing the external ventricle drainage in the anatomical structure or a surface of the anatomical structure;

determining entry point data which describes the position of an entry point of the external ventricle drainage on the surface of the anatomical structure based on the mapping data and the spatial relationship data, wherein the position of the entry point is determined as a surface distance on the 3D skin model of the patient's head in an orthogonal relationship to a line extending from a bregma to a nasion in the patient's coordinate system; and preparing for output presentation to a user the visualization of the determined entry point data for placement of the external ventricle drainage, wherein the at least one computer is operably coupled to the at least one medical imaging device for acquiring, from the at least one medical imaging device, the patient image data.

* * * * *